United States Patent [19]
Guenther et al.

[11] Patent Number: 5,500,884
[45] Date of Patent: Mar. 19, 1996

[54] DENTAL X-RAY DIAGNOSTIC INSTALLATION FOR PRODUCING PANORAMA X-RAY EXPOSURES OF THE SKULL OF A PATIENT

[75] Inventors: Werner Guenther, Benscheim; Dieter Molitor, Buerstadt; Leonhard Werner, Hemsbach, all of Germany

[73] Assignee: Siemens Aktiengesellschaft, Munich, Germany

[21] Appl. No.: 382,210

[22] Filed: Feb. 1, 1995

[30] Foreign Application Priority Data

Feb. 14, 1994 [DE] Germany .................. 44 04 640.5

[51] Int. Cl.⁶ .................................................. A61B 6/14
[52] U.S. Cl. ..................................... 378/38; 378/197
[58] Field of Search ................... 378/38–40, 196, 378/197

[56] References Cited

U.S. PATENT DOCUMENTS

4,419,764  12/1983  Kinanen ......................... 378/40
4,811,372  3/1989  Doebert et al. .

Primary Examiner—Craig E. Church
Attorney, Agent, or Firm—Hill, Steadman & Simpson

[57] ABSTRACT

A dental x-ray diagnostics installation for producing panorama x-ray exposures of the skull of a patient has a rotary unit and a positioning unit mounted so as to be pivotable boom-like around a horizontal axle shaft and are arranged so as to be fixable in individual swiveled positions. The individual swiveled positions thereby correspond to different physical sizes of a seated patient. For preparing an exposure, the positioning unit is first adjusted to the patient and the rotary unit is subsequently adjusted in a fixed allocation to the positioning unit.

14 Claims, 7 Drawing Sheets

DENTAL X-RAY DIAGNOSTIC INSTALLATION FOR PRODUCING PANORAMA X-RAY EXPOSURES OF THE SKULL OF A PATIENT

BACKGROUND OF THE INVENTION

1. Field of the Invention

The present invention is directed to an x-ray diagnostic installation for producing images for dental diagnostics, and in particular to such an installation of the type suitable for producing x-ray images of a patient's skull.

2. Description of the Prior Art

Dental x-ray diagnostic installations are disclosed, for example, in European Application 0 229 308 and U.S. Pat. No. 4,811,372. Such installations include a rotary unit movable around the patient's head and at which an x-ray source and an x-ray pick-up unit are held diametrically opposite one another. In these known installations, the rotary unit is annularly fashioned and is mounted so as to be height-adjustable on an upright column. The rotary unit contains a rotatable part at which the radiation source and pick-up unit (film cassette) are held and contains a carrier part is fixed relative thereto, which is height-adjustable at column and which is also hinged pivotably around a point deviating from the center of rotation. The installation further contains a positioning unit that fixes the patient's head in a reproducible way in a known manner and which is usually composed of a skull holder that fixes the forehead and temples of the patient and which has a bite-down part or a chin support.

SUMMARY OF THE INVENTION

It is an object of the present invention to provide an x-ray diagnostic installation suitable for use in producing dental panorama exposures, which is more economic to manufacture and use and which occupies less space than conventional installations of this type.

The above object is achieved in accordance with the principles of the present invention in an x-ray dental diagnostic installation for producing panorama exposures of the skull of a patient wherein the rotary unit and the positioning unit are carried on a boom-like arrangement so as to be supported in a cantilevered manner from a horizontal shaft. The rotary unit and the positioning unit can thereby be swiveled around said shaft through a number of swivel positions respectively corresponding to different sizes of patients. The positioning unit is first moved to one of these swivel positions relative to a patient, preferably a seated patient, and the rotary unit is subsequently moved to a position having a fixed allocation relative to the positioning unit.

The invention is based on the perception that practically all physical patient sizes can be covered, preferably with the patient seated, solely on the basis of a swiveling motion of the rotary and positioning unit that is held (supported) in the manner of a boom (cantilevered) for example at a wall. It has been found that the differences between small patients having a height of approximately 1.50 m and tall patients having a height of approximately 2 m, when those patients are seated produce adjustment differences, which must be accommodated by swiveling the rotary unit, that amount to only approximately 100–150 mm. Even in the case of small children, the difference amounts to a maximum of only 250 mm. This adjustment path can be implemented by a swivel motion of the rotary and positioning unit without this being bothersome for the patient. An extremely small placement area for the overall installation is required overall given non-use when the rotary and positioning unit is pivoted away from its working position, such as moving it against a wall on which it is mounted. The installation can thus be accommodated, in particular, given extremely small space conditions.

As a result of being coupled to an x-ray diagnostics apparatus for producing what are referred to as intra-oral exposures, i.e. with an x-ray pick-up unit (film or sensor) that can be placed intra-orally, a universal utilization can be achieved given common utilization of the power supplies and control electronics. A complete x-ray station for exposures of individual teeth and for panorama exposures of the jaw can be produced in a way that is space-saving and is also technologically simpler, and thus more cost-efficient as a result of these measures.

DESCRIPTION OF THE PREFERRED EMBODIMENTS

Figure 1:
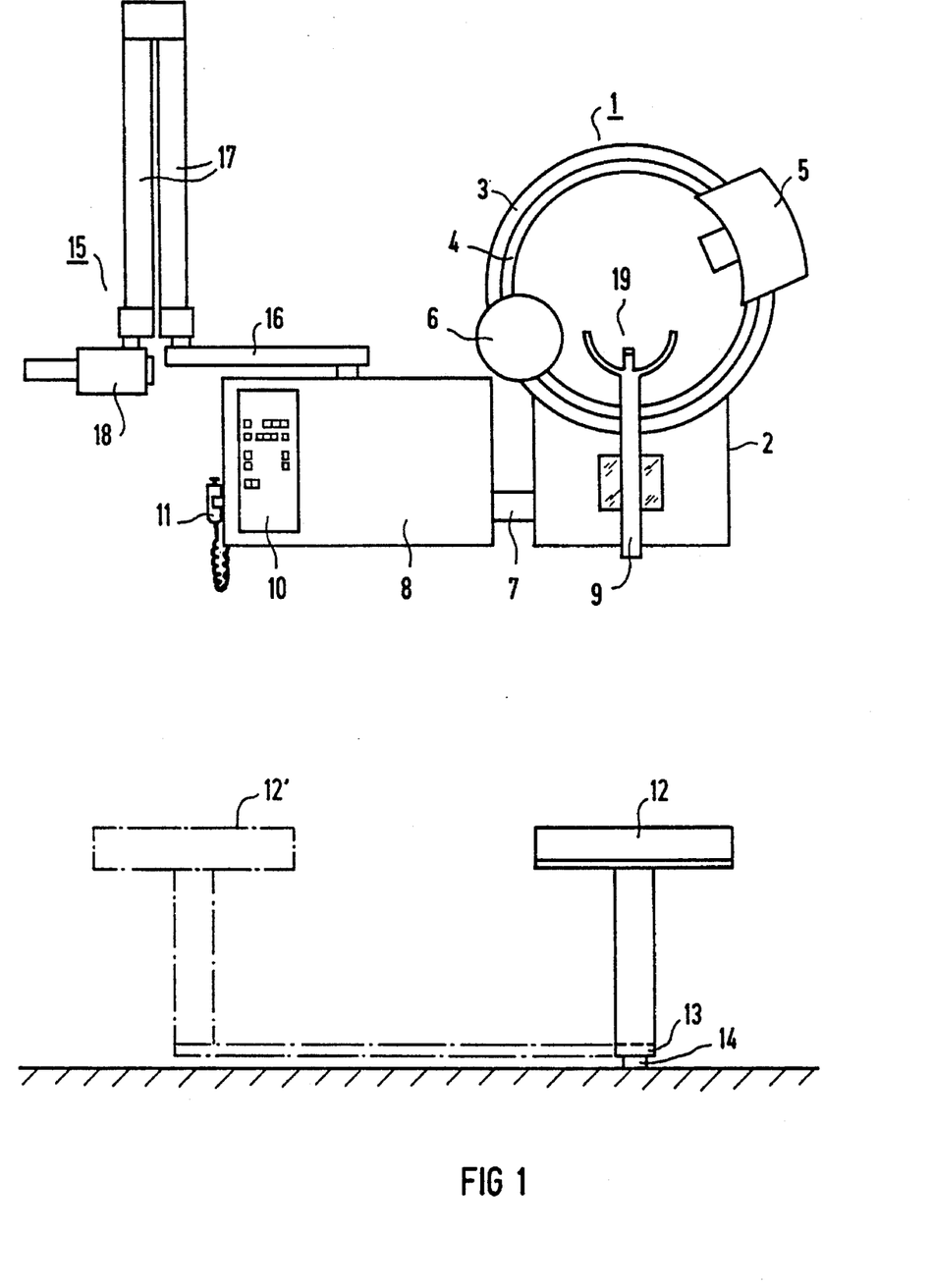
FIG. 1 is a first embodiment of the basic equipment of the x-ray diagnostics installation of the invention shown in a front view.

FIG. 1 shows a first embodiment of the installation of the invention in a front view. The basic equipment (which can be augmented) includes only an x-ray apparatus for producing panorama tomograms of the skull of a patient. This x-ray apparatus contains a rotary unit I which, in a known way, has a first (outer) ring connected to a carrier 2 and at which a second (inner) ring 4 arranged rotatably relative thereto is held. A radiator (x-ray source) 5 as well as an x-ray pick-up unit 6 are held at the second ring 4 diametrically opposite one another. As shown in FIG. 1, the pick-up unit 6 can be a rotatable film drum that has a flexible film cassette; given a digital x-ray means, a CCD line sensor can also be provided instead of the film drum. During a panorama exposure, the second ring 4 is turned around the axis of its mid-point, i.e., the radiator and film cassette orbit the patient's head, whereas the first ring 3 is pivoted around a pivot point located outside the mid-point. Control of the drives in a manner for producing a tomographic exposure is known, and need not be discussed in greater detail.

Figure 3:
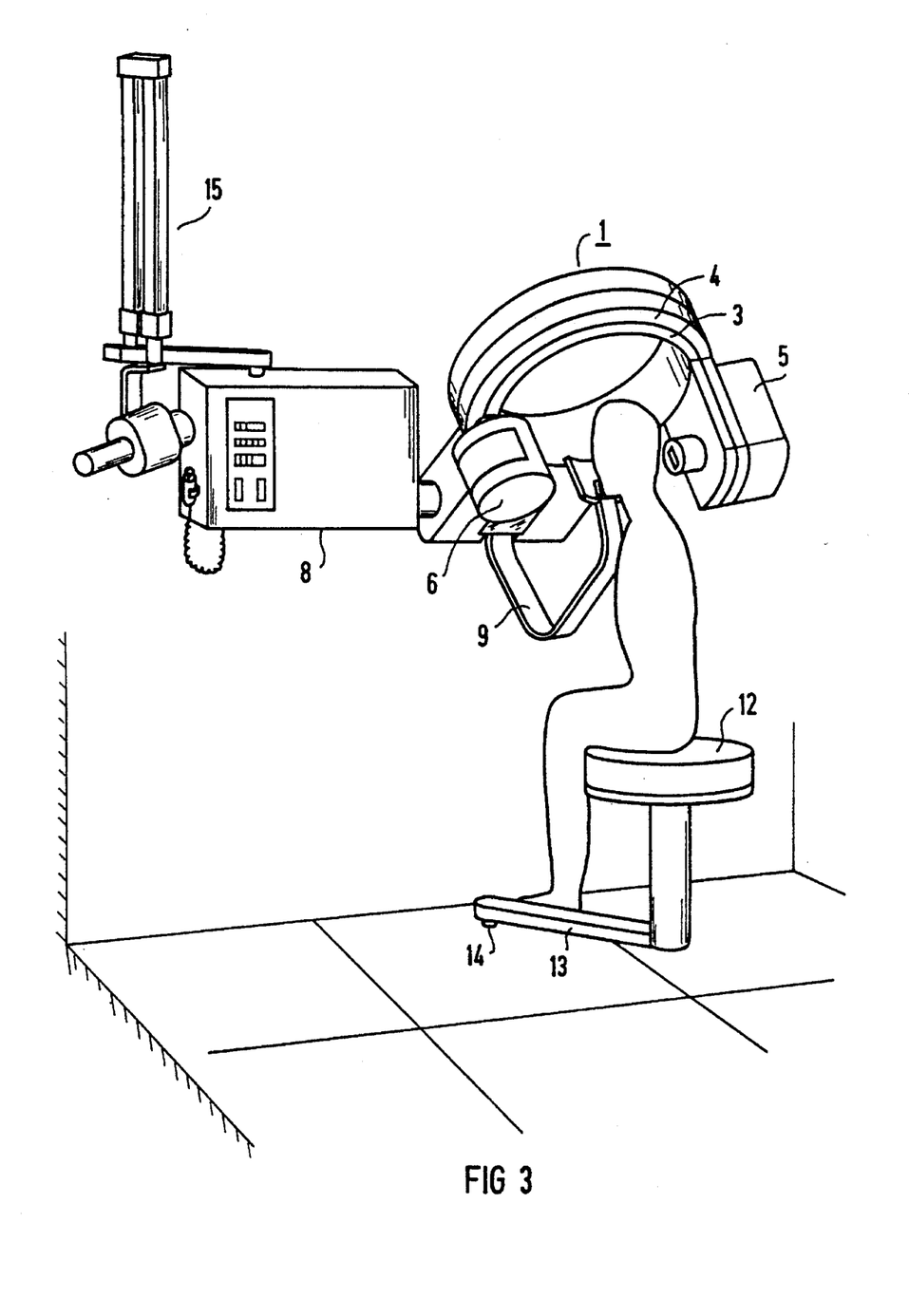
FIG. 3 shows the installation of FIG. I shown in a second user position.
Figure 4:
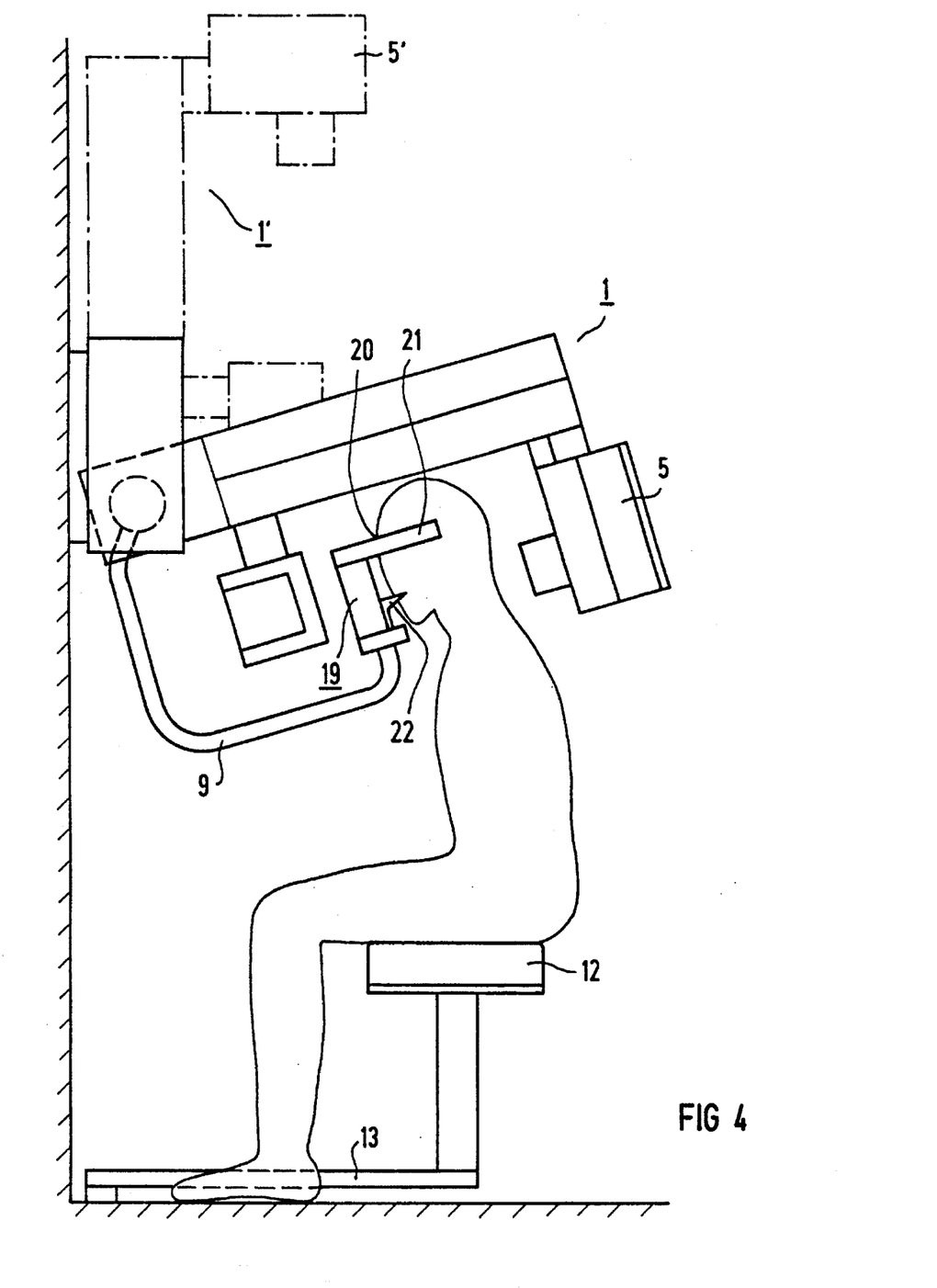
FIG. 4 is a schematic illustration of a user position similar to that shown in FIG. 3.

The rotary unit I is shown in a non-use position in FIG. 1 wherein the radiator 5 and pick-up unit 6 come to lie in a vertical plane, i.e. parallel to the wall. The rotary unit 1 can be brought into various user positions by means of a swiveling shaft 7 (FIGS. 3 and 4). To this end, the swiveling shaft 7 is correspondingly seated in a housing 8 that can be secured to a wall. Further details regarding this can be seen in FIGS. 5 and 6 together with the description below.

A positioning unit 9 is pivotably seated in the carrier 2 isoaxially with the swiveling shaft 7, but adjustable separately therefrom. The positioning unit 9 contains suitable means for reproducibly fixing the patient's head with reference to the middle of the face and the Frankfurt horizontal. A mirror (not shown) at the carrier can serve as an adjustment aid. The aforementioned means are advantageously a skull holder 19 of plexiglass or of similar transparent material that surrounds the front side of the patient's head, and which carries an adjustable forehead support 20 having temple supports 21 that can be laterally placed against the patient's head as well as an interchangeable bite-down plate 22 for fixing the front teeth of the patient (FIG. 4).

At its front side, the housing 8 contains a display and operating panel 10 having various switch and/or display elements. A hand-held activation switch 11 is provided with which the radiator 5 is activated by an operator to emit x-rays and with which, thus, an exposure can be triggered.

The above-described x-ray apparatus has a patient chair 12. The chair 12 is arranged with reference to the x-ray apparatus by means of a swivel arm 13 and an axle bearing 14 located wall-proximate so that a patient seated on the chair in the user position can be positioned relative to the rotary unit 1. As may be seen from the dot-dashed illustration, the chair 12 can be brought into a swiveled position (12') around the axle bearing 14 wherein—using the basic apparatus already described—what are referred to as intra-oral exposures can be made by augmenting the basic apparatus with a second x-ray apparatus 15 that is likewise held at the housing 8. A possible user position for such an intra-oral exposure is schematically illustrated in FIG. 2.

The x-ray apparatus 15 held at the housing 8 contains a swivel arm 16 to which a double-hinged arm 17 is hinged, at whose free end an x-ray source 18 is hinged in a known way. When intra-oral exposures are made in the user position shown in FIG. 2, the rotary unit I of the basic x-ray apparatus is located in the non-use positions shown in FIGS. 1 and 2.

Figure 2:
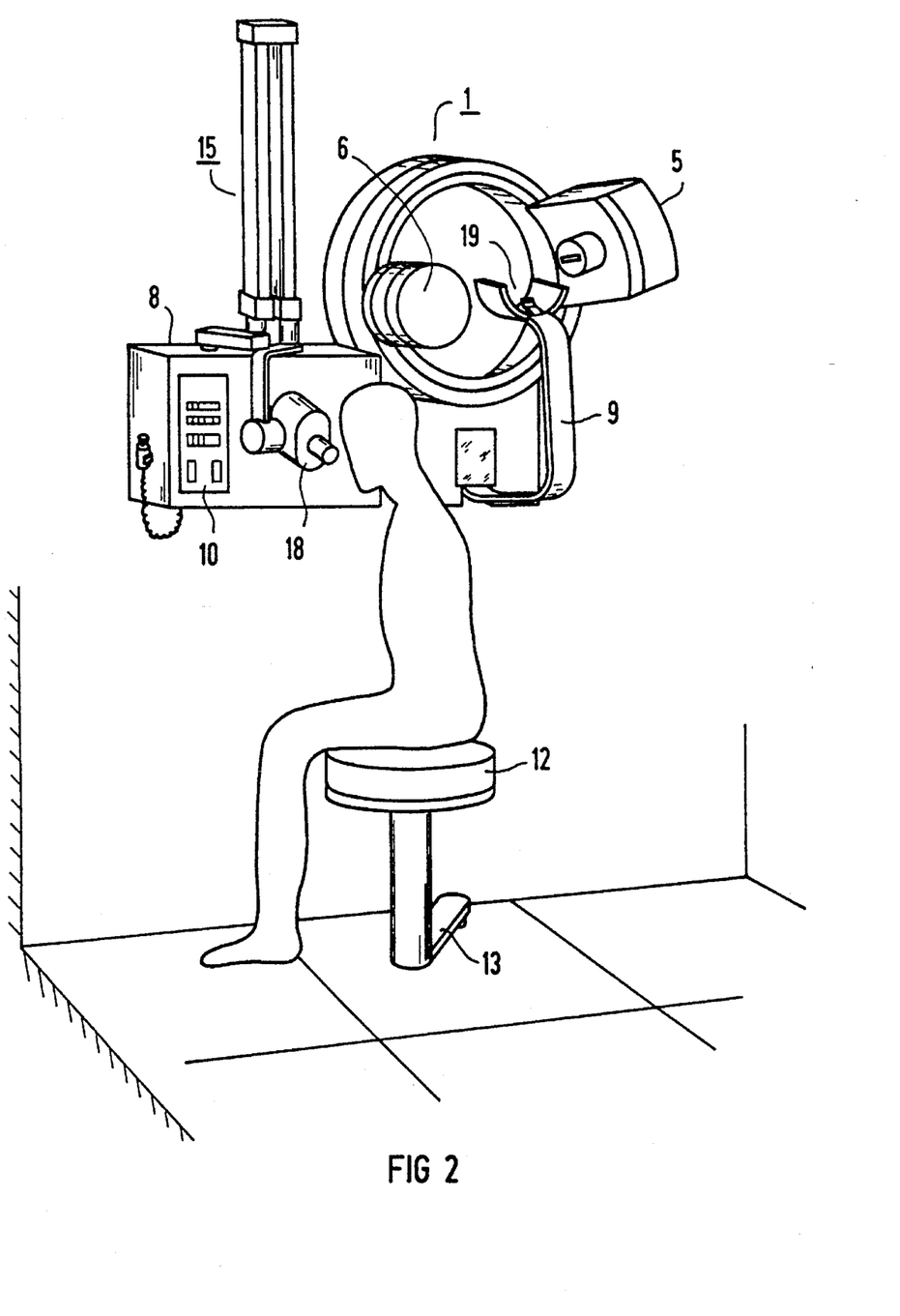
FIG. 2 shows the installation of FIG. 1 in a perspective illustration in a first user position.

For producing panorama exposures, the rotary unit 1 can be brought from the storage (non-use) position shown in FIGS. 1 and 2 into various user positions as shown, for example, in FIGS. 3 and 4. To this end, the rotary unit I and the positioning unit 9 are swiveled by a specific angle. The swivel angle is predetermined by the head height of the patient to be diagnosed when he or she has been seated on the patient chair 12. For preparing for an exposure, the positioning unit 9 is first swiveled to such an extent that the patient's head can be exactly positioned in the skull holder 19. After this, the rotary unit 1 is likewise swiveled, to such an extent that the rotary unit I this resides in a fixed allocation to the positioning unit 9 or to the skull holder 19. This allocation of rotary unit 1 and positioning unit 9 is established for every patient setting, so that an exact transirradiation of the skull corresponding to the previously-fixed patient head is always established regardless of whether a tall or short patient is seated on the chair. The positioning unit 9 can be fixed in the swiveled position matched to the respective patient with, for example, a magnetic brake or with some other suitable means. Mechanical and/or electrical coupling and catch means can be provided for this purpose, as shown in the exemplary embodiment in FIG. 6.

FIG. 4 shows a simplified illustration of the rotary unit 1 in a side view. The storage position (dot-dashed lines), as well as one of a plurality of possible user positions and the allocation thereof to the patient may be seen from the illustration.

Figure 5:
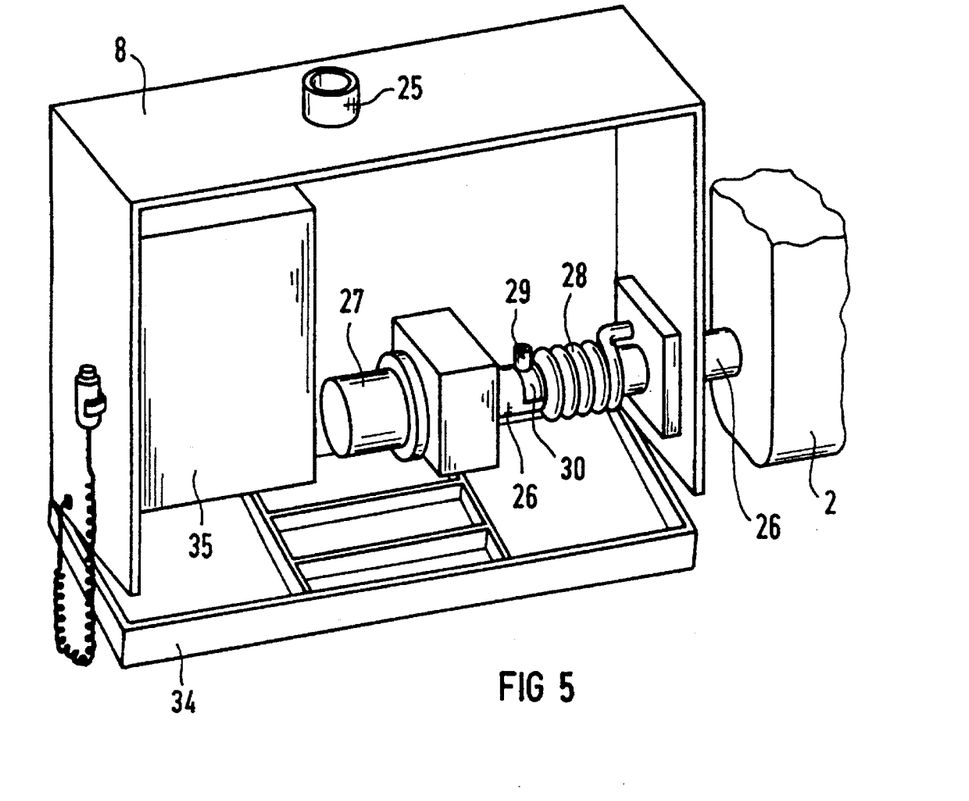
FIGS. 5 and 6 show details of the installation housing that can be secured to a wall.

FIG. 5 shows a schematic illustration of the housing 8 with the front wall removed. A bearing bushing 25 for accepting the swivel arm 16 is located at the upper side of the housing 8. The swiveling shaft 7, which is torsionally connected to the carrier 2, is rotatably seated in a bearing tube 26 and can be turned with the assistance of a schematically shown motor drive 27. The drive 27 can be advantageously composed of a stepping motor and a corresponding transmission gearing. A torsion spring 28 is arranged on the bearing tube 26 concentrically relative to the swiveling shaft 7; one end of this torsion spring 28 being connected to the swiveling shaft via a dog 29 and the other end thereof being supported at the housing 8. The torsion spring 28 serves the purpose of weight compensation and is dimensioned such that the entire rotary unit 1 is weight-counter balanced in every swiveled position. As a result, the drive 27 can be dimensioned extremely small.

The dog 29 is secured to the swiveling shaft 7 and extends through a slot 30 in the bearing tube 26; it clamps the aforementioned one end of the torsion spring 28 against the swiveling shaft 7 as well as forming a detent together with the ends of the slot.

Figure 6:
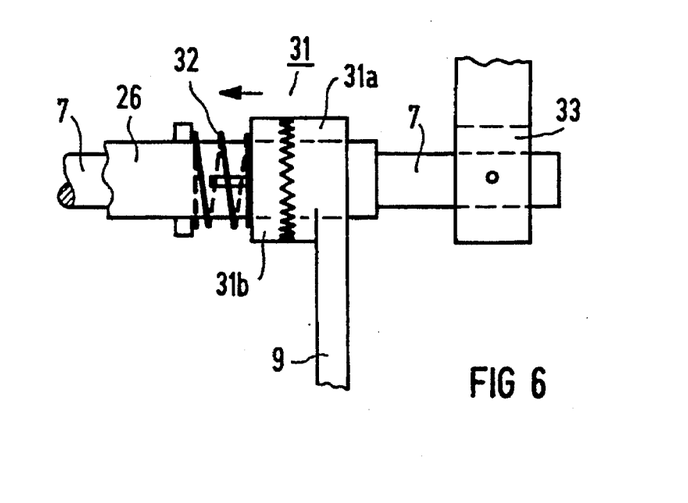

The bearing tube 26 extends into the housing 8 of the carrier 2 and contains a latchable coupling 31 for the positioning unit 9, that is shown in terms of a mechanical embodiment in FIG. 6. The coupling 31 is composed of two crown gears 31a and 31b, one (31a) thereof being rotatably arranged at the bearing tube 26 and being firmly connected to the positioning unit 9, and the other (31b) being guided torsionally but axially at the bearing tube 26 and being arranged so as to be capable of being disengaged in the arrow direction opposite the force of a spring 32, by means of a disengagement lever (not shown). For adjusting the positioning unit 9 relative to the patient, the crown gear 31b is first disengaged in the arrow direction, which permits the positioning unit 9 to be brought into a user position matched to the patient. After this, the rotary unit 1 can be set to this position with the assistance of the drive 27. To this end, the carrier 2 is connected to the shaft 7 via, for example, a fork-shaped dog 33.

The base of the housing is advantageously fashioned as a hingable compartment 34 and is provided with various subdivisions so that accessory parts or the like allocated to the x-ray apparatus can be stored therein.

Figure 7:
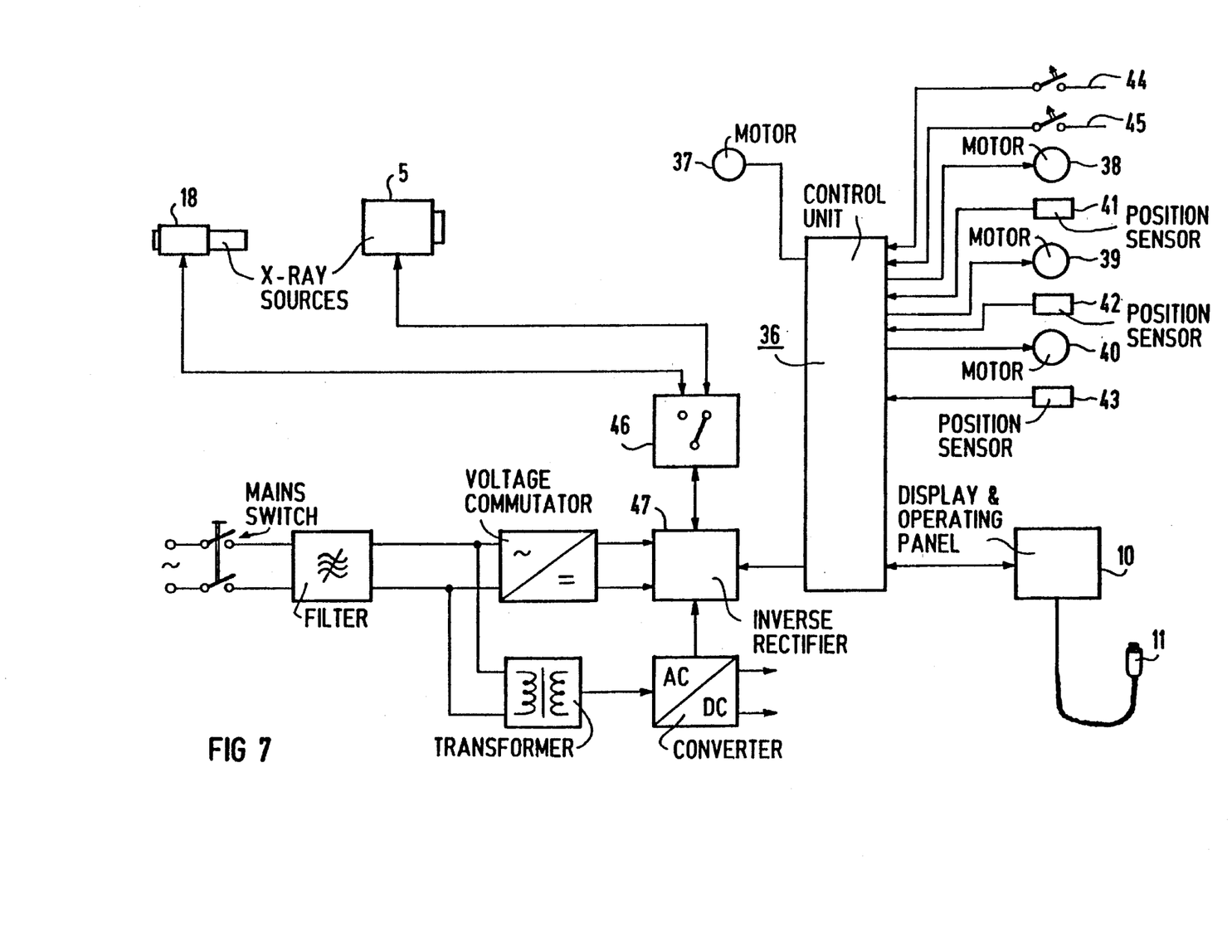
FIG. 7 is a block circuit diagram of the installation of the invention.

A control unit 35 is also accommodated in the inside of the housing 8, this control unit 35 containing the electronics for driving the existing drives as well as for driving the two x-ray sources according to the block circuit diagram of FIG. 7.

FIG. 7 shows a block circuit diagram of the above-described system. The control unit 35 contains central control electronics 36 having a microprocessor by means of which four adjustment motors 37–40 are controlled. The first of these adjustment motors serves the purpose of tilting the overall rotary unit 1; the second initiates the rotation of the rotatable ring 4; the third effects the rotation of the film cassette; and the fourth serves for effecting the described swivel motion of the non-rotatable part of the ring in the horizontal plane. The adjustment motors are advantageously stepping motors.

Position sensors 41–43 are provided, which obtain and supply information about the starting position, the rotary ring 4, the film cassette and the swiveled position of the rotary ring 4. These positional sensors can, for example, be formed as light barriers sensors. The non-use position as well as the user position of the rotary unit are acquired by sensors 44 and 45, which may be microswitches or light barriers; the different drive of the radiation sources 5 and 18 ensues with a switch-over unit 46 that connects the output of an inverse rectifier 47 to the radiation source 5 or 18, dependent on which x-ray apparatus is being utilized. The switching can ensue automatically based on signals from the sensors 44 and 45 or can be manually implemented.

The remaining component parts of the control unit 35 such as a mains switch, a mains rectifier, a voltage commutator and a voltage converter are not shown in detail since they are standard components.

Figure 8:
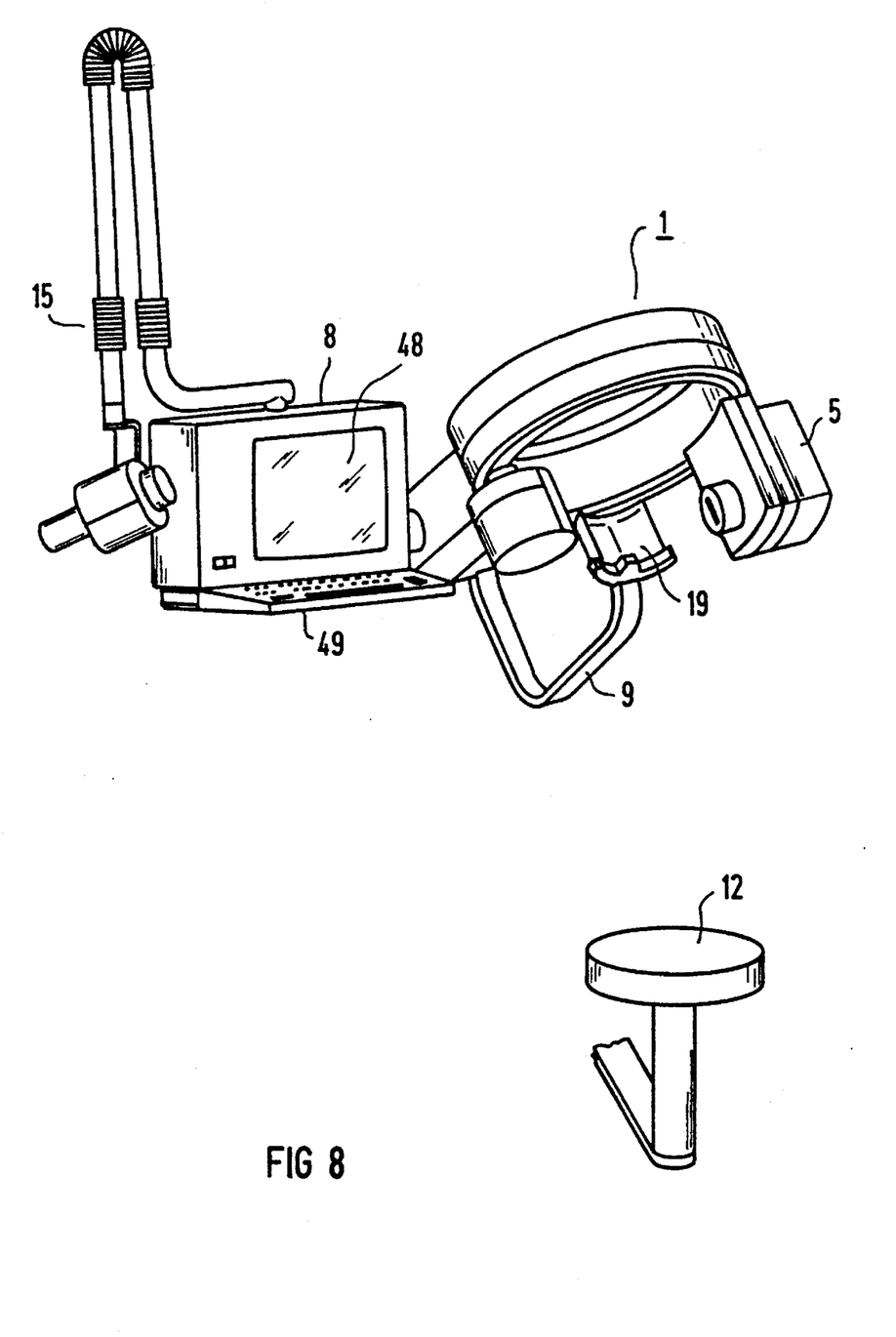
FIG. 8 is a schematic illustration of a further version of an installation of the invention.

FIG. 8 shows a further embodiment of the basic apparatus of the invention. In this version, the housing 8 contains a flat picture screen 48 at the front side and contains an input keyboard 49. Such a combination is advantageous particularly given an x-ray apparatus having digital image processing, wherein an x-ray-sensitive sensor having corresponding image processing is provided instead of a film cassette.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray dental diagnostic installation for producing panorama exposures of the skull of a patient, comprising:

an x-ray source;

an x-ray pick-up unit;

rotary means, on which said x-ray source and said x-ray pick-up unit are mounted opposite each other, for rotating said x-ray source and said x-ray pick-up unit around the head of a patient;

positioning means for reproducibly fixing a position of the head of said patient;

boom means, including a horizontal shaft, for supporting said rotary means and said positioning means cantilevered from said shaft and for permitting swiveling of said rotary means and said positioning means around said shaft through a plurality of swiveled positions respectively corresponding to different sizes of patients for initially positioning said positioning means in one of said swivel positions relative to a patient and for subsequently positioning said rotary unit in a fixed position allocated to the position of said positioning means; and means for operating said x-ray source and said x-ray pick-up unit to produce a panorama tomogram of the head of said patient with said positioning means in said one of said swivel positions and said rotary means in said fixed position.

2. An x-ray dental diagnostic installation as claimed in claim 1, wherein said boom means comprises means for moving said rotary unit and said positioning unit from a storage position wherein said radiation source and said pick-up unit are disposed substantially in a vertical plane into said plurality of swivel positions, said radiation source and said pick-up unit forming a respective acute angle relative to said vertical plane in each of said swivel positions.

3. An x-ray dental diagnostic installation as claimed in claim I for use with a stable vertical surface, and further comprising a housing containing said shaft and being adapted for mounting on said stable vertical surface, and wherein said housing also contains said means for operating said x-ray source and said x-ray pick-up unit.

4. An x-ray dental diagnostic installation as claimed in claim I wherein said shaft is rotatably mounted in said housing, and further comprising a torsional connection between said rotary unit and said shaft.

5. An x-ray dental diagnostic installation as claimed in claim 4 wherein said rotary unit is torsionally connected to said shaft by a torsion spring surrounding said shaft and having one end attached to said housing and an opposite end attached to said shaft.

6. An x-ray dental diagnostic installation as claimed in claim 4 wherein said rotary unit is torsionally connected to said shaft by a torsional, axially displaceably coupling disposed between said shaft and said positioning means.

7. An x-ray dental diagnostic installation as claimed in claim 3 wherein said housing has a base, and said housing further comprising a storage compartment contained in said housing and accessible through said base.

8. An x-ray dental diagnostic installation as claimed in claim 3 further comprising additional x-ray means for producing intra-oral exposures, and bearing means contained in said housing for pivotably holding said additional x-ray means.

9. An x-ray dental diagnostic installation as claimed in claim 8 further comprising a patient seat mounted on a swivel arm for supporting a patient both for the production of said panorama exposure and for the production of said intra-oral exposure.

10. An x-ray dental diagnostic installation as claimed in claim 9 wherein said further x-ray apparatus includes a further x-ray source, and wherein said x-ray dental diagnostic installation further comprises common control means for operating both the radiation source for producing panorama exposures and the further radiation source for producing intra-oral exposures.

11. An x-ray dental diagnostic installation as claimed in claim 10 further comprising switch means for switching said common control means for operating said radiation source or said further radiation source, dependent on the position of said boom means.

12. An x-ray dental diagnostic installation as claimed in claim 1 wherein said positioning means comprises a head holder having an adjustable forehead support, temple supports adapted for placement against the head of the patient, and a bite-down plate for fixing the position of the front teeth of the patient.

13. An x-ray dental diagnostic installation as claimed in claim 1 wherein said x-ray pick-up unit comprises a digital image pick-up unit, wherein said means for operating said x-ray source and said x-ray pick-up unit to produce a panorama exposure includes image evaluation means for digitally processing signals from said digital image pick-up and for producing a digital image therefrom, and further comprising an image display to which said digital image is supplied.

14. An x-ray dental diagnostic installation as claimed in claim 13 further comprising a housing containing said means for operating said x-ray source and said x-ray pick-up unit, and wherein said display is disposed at said housing.

* * * * *